(12) United States Patent
Mistral

(10) Patent No.: US 9,176,082 B2
(45) Date of Patent: Nov. 3, 2015

(54) MEASURING THE DAMAGE TO A TURBINE-BLADE THERMAL BARRIER

(75) Inventor: Quentin Mistral, Montrouge (FR)

(73) Assignee: SNECMA, Paris (FR)

( * ) Notice: Subject to any disclaimer, the term of this patent is extended or adjusted under 35 U.S.C. 154(b) by 323 days.

(21) Appl. No.: 13/700,290

(22) PCT Filed: May 27, 2011

(86) PCT No.: PCT/FR2011/051227
§ 371 (c)(1),
(2), (4) Date: Nov. 27, 2012

(87) PCT Pub. No.: WO2011/151582
PCT Pub. Date: Dec. 8, 2011

(65) Prior Publication Data
US 2013/0077649 A1    Mar. 28, 2013

(30) Foreign Application Priority Data

Jun. 3, 2010 (FR) ...................... 10 54371

(51) Int. Cl.
*G01N 25/72* (2006.01)
*F01D 5/28* (2006.01)
*G01N 17/00* (2006.01)

(52) U.S. Cl.
CPC ................ *G01N 25/72* (2013.01); *F01D 5/288* (2013.01); *G01N 17/006* (2013.01)

(58) Field of Classification Search
USPC ........................ 374/1, 5, 57, 120, 7
See application file for complete search history.

(56) References Cited

U.S. PATENT DOCUMENTS

| | | | | |
|---|---|---|---|---|
| 5,238,752 A | * | 8/1993 | Duderstadt et al. | 428/623 |
| 5,512,382 A | * | 4/1996 | Strangman | 428/632 |
| 5,683,825 A | | 11/1997 | Bruce et al. | |
| 5,900,102 A | * | 5/1999 | Reeves | 156/701 |
| 6,123,997 A | * | 9/2000 | Schaeffer et al. | 427/383.7 |

(Continued)

FOREIGN PATENT DOCUMENTS

| | | |
|---|---|---|
| EP | 0 783 043 | 7/1997 |
| EP | 1 494 020 | 1/2005 |

(Continued)

OTHER PUBLICATIONS

International Search Report Issued Sep. 27, 2011 in PCT/FR11/51227 Filed May 27, 2011.

*Primary Examiner* — Mirellys Jagan
(74) *Attorney, Agent, or Firm* — Oblon, McClelland, Maier & Neustadt, L.L.P.

(57) ABSTRACT

A method for evaluating damage to a thermal barrier applied to a component made from a metal substrate, the thermal barrier including a sublayer of aluminum and a layer of columnar-structure ceramic material, the sub-layer being positioned between the substrate and the ceramic layer, the method including: a first calibration including selection of a determined number of calibration components that have undergone various degrees of damage, exposing them for a given length of time to radiation, measuring temperature obtained at the surface after the given length of time and establishing a curve connecting an increase in temperature to damage, and a second measuring the damage to the thermal barrier of the component including exposure to the radiation for the length of time, measuring the temperature obtained, and relating the increase in temperature to the calibration curve in order, from the curve, to extract the level of damage.

7 Claims, 2 Drawing Sheets

(56) References Cited

U.S. PATENT DOCUMENTS

| | | |
|---|---|---|
| 6,355,356 B1 * | 3/2002 | Hasz .......................... 428/472 |
| 2002/0122457 A1 * | 9/2002 | Sasajima et al. ................. 374/2 |
| 2003/0115941 A1 * | 6/2003 | Srivastava et al. .......... 73/118.1 |
| 2004/0179575 A1 * | 9/2004 | Markham ..................... 374/121 |
| 2005/0153160 A1 * | 7/2005 | Liu et al. ...................... 428/633 |
| 2008/0261073 A1 * | 10/2008 | Maloney et al. .............. 428/680 |
| 2009/0162533 A1 * | 6/2009 | Kirby et al. ...................... 427/8 |
| 2009/0312956 A1 | 12/2009 | Zombo et al. |
| 2009/0316748 A1 * | 12/2009 | Wawrzonek et al. ........... 374/46 |
| 2011/0189379 A1 | 8/2011 | Ortner et al. |

FOREIGN PATENT DOCUMENTS

| | | |
|---|---|---|
| EP | 1 852 697 | 11/2007 |
| WO | 2009 118199 | 10/2009 |

\* cited by examiner

MEASURING THE DAMAGE TO A TURBINE-BLADE THERMAL BARRIER

BACKGROUND OF THE INVENTION

1. Field of the Invention

The field of the present invention is that of turbine engines and, more particularly, that of the lifetime of the components of these turbine engines which are subjected to high temperatures.

2. Description of the Related Art

The components of the hot parts of a turbine engine and, in particular, the turbine blades are subjected in use to extremely high temperature conditions and protections have been conceived to enable them to withstand these extreme conditions. Amongst the latter is included the deposition of a coating, called thermal barrier, on their external face, which protects the metal in which they are formed. A thermal barrier is generally composed of a ceramic layer of around a hundred microns, which is deposited perpendicularly to the surface of the metal layer. An underlayer made of aluminum, of a few tens of microns, placed between the ceramic and the metal substrate, completes the thermal barrier by providing the bond between these two components together with the protection of the metal of the blade against oxidation.

Ceramic has the drawback of only having a low thermal expansion, whereas the substrate that forms the blade is made of a metal of the superalloy type which has a high thermal expansion coefficient. The difference in thermal expansion is compensated by the formation of the ceramic in a columnar form, since the columns can separate from one another in order to adapt to the new width of the substrate.

One of the consequences of this is that oxygen, which is present in the gas flowing in the jetstream of the turbine engine, comes into contact with the aluminum of the underlayer and progressively oxidizes it. Aging of the thermal barrier is thus observed, which depends on the thickness of the layer of alumina produced. When it reaches a certain level of damage, the aluminum underlayer no longer fulfils its function of elasticity, delaminations appear and flaking of the thermal barrier occurs. The metal of the substrate is then no longer protected and the blade is in danger of being very rapidly degraded.

It is therefore important to know the level of damage to the thermal barrier and to forestall the appearance of this flaking. Many techniques have been conceived for monitoring the state of the thermal barrier and to know whether it is possible to maintain a blade in use. Amongst the latter, visual inspection, which only detects a defect when flaking has already occurred, infrared thermography or again piezospectroscopy are known. IR thermography has until now been used, as is the case for the patent application EP 1494020, only for detecting delaminations in the aluminum underlayer, which are precursors to the flaking, by the fact that they modify the local thermal properties of the product. However, it only works when a defect has already appeared. Piezospectroscopy measures the stress existing at the interface between the ceramic thermal barrier and the aluminum underlayer. As long as the thermal barrier adheres to the part, a stress is measured at this interface and it is known that the barrier is sound, whereas the absence of stress corresponds to the appearance of a fissure at this interface. Here again, the detection only takes place after the appearance of a defect.

The existing methods, which only work by detection of a defect, do not allow the remaining lifetime of a component to be forecast, nor an intervention on it before the damage becomes too severe.

BRIEF SUMMARY OF THE INVENTION

The aim of the present invention is to overcome these drawbacks by providing a method for measuring the aging of a thermal barrier which is not based on the prior appearance of a defect.

For this purpose, the subject of the invention is a method for evaluating the damage to a thermal barrier deposited on a component formed in a metal substrate, said thermal barrier comprising an aluminum underlayer and a layer of ceramic material with a columnar structure oriented perpendicularly to said substrate, said underlayer being positioned between said substrate and said ceramic layer, said component being designed to be placed in use in contact with an oxidizing gaseous medium and generator of said damage by oxidation of said underlayer, said damage being defined by the thickness of oxidized metal present in said underlayer, characterized in that it comprises a first calibration step comprising at least the following sub-steps:

- selection of a given number of calibration elements formed in said substrate and covered by said thermal barrier, said elements having been subjected to damage by exposure for different periods of time to oxidation conditions representative of said use,
- exposure, for a given period of time, of said calibration elements to an electromagnetic radiation,
- measurement of the temperature obtained on the surface after the given time, for each calibration element,
- establishment of a calibration curve relating the measured increase in temperature to the damage suffered, and a second step for measuring the damage to the thermal barrier of said element comprising the following sub-steps:

- exposure to said radiation of the element to be evaluated for said period of time,
- measurement of the temperature obtained on the surface after said given time,
- plot of the measured increase in temperature after said given time onto the calibration curve, and
- extraction of the damage from said calibration curve.

The rise in the temperature under the action of the radiation applied for a given period of time is indicative of the thickness of the layer of alumina which has been formed in the course of the successive damages suffered by the component to be evaluated. By means of a calibration carried out on samples for which there is prior knowledge of the damage, the damage suffered by the thermal barrier of a component may be determined by only reading the increase in temperature observed.

Preferably, the radiation is optical radiation in the visible range. In this range of frequencies, the ceramic layer is transparent and the heating means act directly on the layer of alumina. Depending on the thickness of the latter, and as a consequence of its insulating ability, the dissipation of the heat in the direction of the substrate may or may not readily take place and hence more or less heat is directed toward the surface of the component to be evaluated.

Advantageously, the radiation is provided by the illumination of at least one halogen lamp. This thus corresponds to a lamp with high radiating power throughout the whole visible range.

Preferably, the measurement of the surface temperature is carried out by a camera operating in the infrared.

The invention relates in particular to the application of the method hereinabove to the measurement of the damage to a turbine blade of a turbine engine.

BRIEF DESCRIPTION OF THE SEVERAL VIEWS OF THE DRAWINGS

The invention will be better understood, and other aims, details, features and advantages of the latter will become more clearly apparent in the course of the detailed explanatory description that follows, of one or more embodiments of the invention presented by way of examples that are purely illustrative and non-limiting, with reference to the appended schematic drawings.

In these drawings.

DETAILED DESCRIPTION OF THE INVENTION

Figure 1:
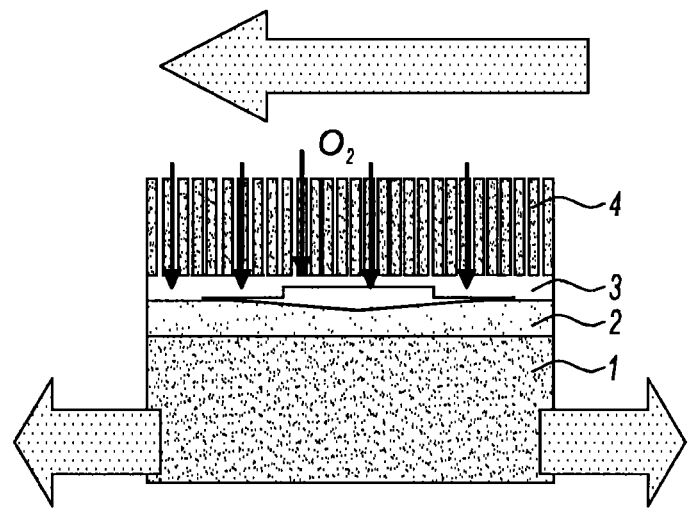
FIG. 1 is a schematic view of the physical composition of a thermal barrier for a turbine blade.

With reference to FIG. 1, a cross-sectional view is seen of the composition of a thermal barrier deposited on the surface of a turbine blade. The metal constituent of the blade, typically a superalloy containing nickel, forms a substrate 1 on which a layer of aluminum 2 is deposited, sandwiched between the substrate 1 and a ceramic layer 4. The function of the layer of aluminum is to give a certain elasticity to the assembly in order to allow it to absorb the difference in thermal expansion existing between the substrate 1 with a high thermal expansion and the ceramic 4 with a low thermal expansion.

The ceramic 4 has a columnar structure, which allows lateral displacements, owing to the appearance of fissures between the columns. However, one of the consequences of this is that the aluminum comes into contact with oxygen carried by the gas flowing in the jetstream of the turbine engine. The layer of aluminum 2 is thus transformed, over a given thickness, into a layer of alumina 3. The thickness of the layer of alumina is a function of the time spent at high temperatures, which constitutes an indicator of the damage suffered by the thermal barrier. The invention consists in providing a technique for measuring the thickness of said layer of alumina 3.

Figure 2:
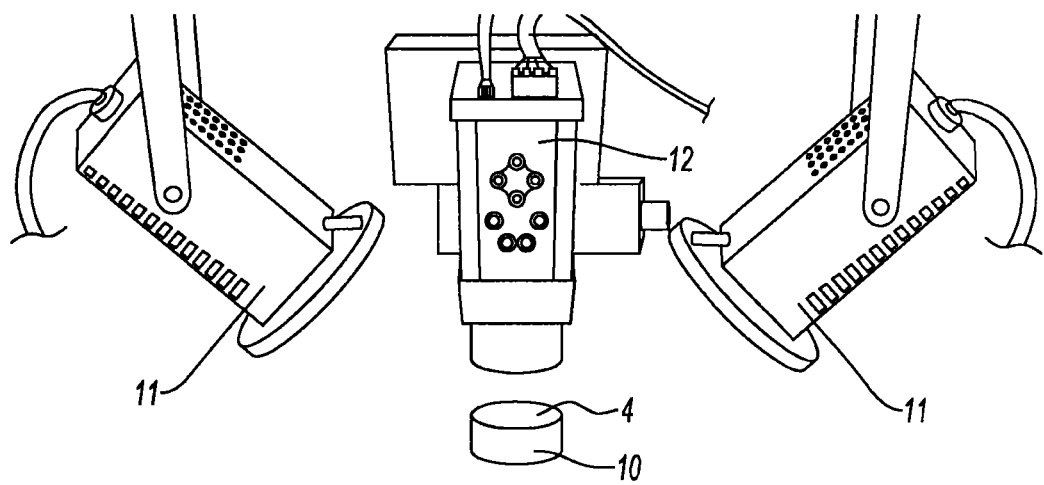
FIG. 2 is a view of one experimental configuration for the implementation of the method, according to the invention, for evaluation of the damage to a thermal barrier.

With reference now to FIG. 2, a device configuration is seen that is capable of being used for the analysis, by means of the method according to the invention, of the damage suffered by a thermal barrier during its lifetime.

The element 10 covered by a thermal barrier, such as described in FIG. 1, whose damage is to be measured is placed facing a heating system 11, shown here in the form of two halogen lamp projectors. A means 12 for measuring the surface temperature of the element 10 is placed opposite it, with which a means for recording (not shown) the variation over time of the measured temperature is associated. In the experiments performed, without this configuration being essential, the measurement means 12 is a thermal camera with a matrix of uncooled bolometers which has a frequency of operation of 50 Hz and a resolution of 320×240.

Figure 3:
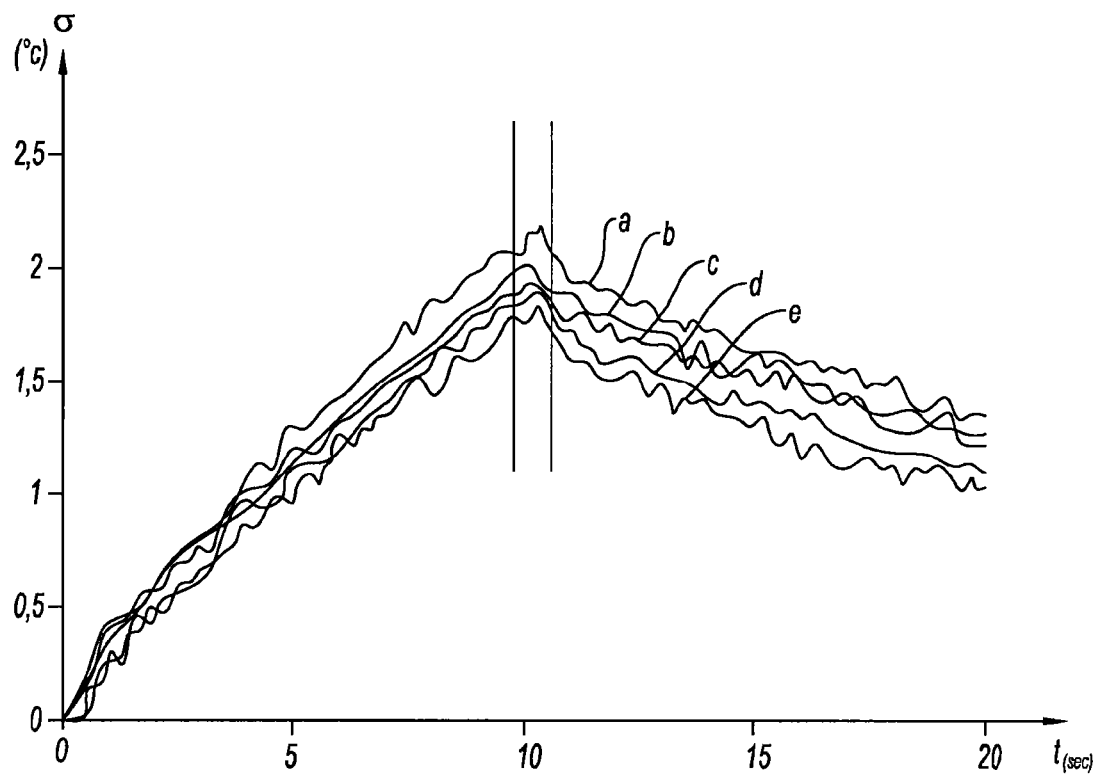
FIG. 3 is a figure showing the variation as a function of time of the surface temperature of several samples, during the implementation of the method according to the invention.

FIG. 3 shows the behavior over time of the surface temperature $\theta$ of the element 10, measured by the device in FIG. 2, while heating for a calibrated period of time (typically 10 seconds) then during the cooling that ensues. This behavior is shown for five samples, referenced from "a" to "e" in the figure, which have the same form of cylindrical pawns and which are covered with a thermal barrier analogous to that which it is desired to evaluate on the blades in service. These five pawns have undergone different aging processes, respectively corresponding to 0, 5, 10, 50 or 100 standard aging cycles for the five curves shown. One aging cycle corresponds to periods of temperature application, followed by periods of cooling, which are supposed to be representative of the damage suffered by the components of a turbine engine during a flight.

The number of cycles to which the various pawns 10 are subjected thus represents a certain number of hours of operation of a turbine blade equipped with the thermal barrier under evaluation. The curve "a", the highest of the five, corresponds to the pawn 10 having the lowest aging, whereas the curve "e", the lowest, corresponds to the pawn with maximum damage. The five curves lie above one another according to their decreasing aging.

Figure 4:
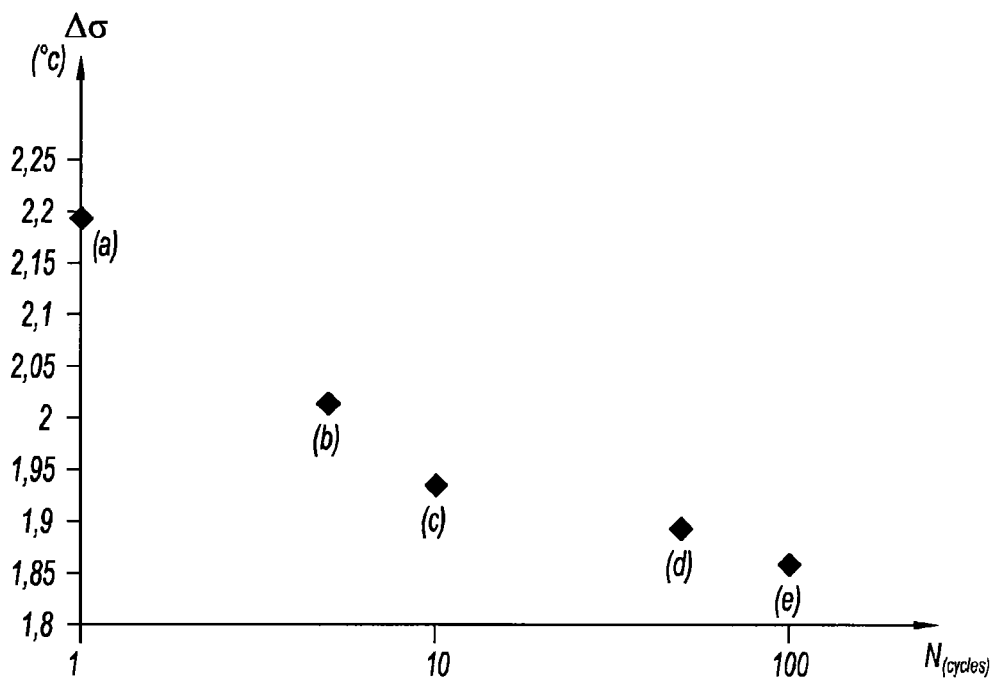
FIG. 4 is a figure showing the relationship between the temperature reached during the implementation of the method according to the invention, and the damage suffered beforehand by the samples evaluated.

FIG. 4 shows on a nomograph the value of the maximum heating $\Delta\theta$ measured by the measurement means 12, after the chosen time for conducting the evaluation on the pawns 10, depending on the number of aging cycles undergone. A regular decrease, and consequently a one-to-one association, is observed between the value of the observed temperature maximum and the number of cycles undergone by the component. One and only one increase in temperature is associated with a number of cycles undergone and, conversely, one number of cycles can be associated with an increase in temperature.

The implementation of the method for evaluating the damage to a thermal barrier according to the invention will now be described, with the device configuration in FIG. 2 and taking for experimental model the pawns 10 described hereinabove.

The process commences by switching on the infrared camera 12 and powering up of the heating means 11. The heating of the pawns 10 is maintained for a predefined duration, such as for example around ten seconds, then is turned off, the pawns then cooling down naturally, as indicated in FIG. 3. During this whole time, the surface temperature of the pawn is measured by the infrared camera 12. By analyzing the recordings made, the value of the maximum temperature reached on the pawn 10 is measured with precision and is plotted on a diagram (cf. FIG. 4) giving the maximum increase in temperature obtained as a function of the number of aging cycles previously undergone by the pawn 10 in question.

By means of the five pawns evaluated, which have different amounts of aging, the method claimed consists in establishing the curve in FIG. 4, in other words the relation existing between the maximum heating observed for a given heating time, and the aging previously undergone. This collection of information may of course be carried out with a larger number of pawns and a greater variety in the number of aging cycles for the pawns, in order to obtain a curve of the maximum heating as a function of the damage that is more precise and whose margin of uncertainty is better known.

Using this curve, it is then possible, by applying heating with the same means 11 to a blade whose state of damage is sought, for a heating time equal to that used for the establishment of the curve, to measure the maximum temperature reached. The damage that it has suffered is then obtained very simply by plotting the measured value on the curve in FIG. 4 and by deducing from this, on the abscissa, the number of cycles undergone. Knowing this number of cycles, it is then easy to deduce from this the remaining lifetime of the component in order to either put it back into service for a given period of time, or to send it for repair in order to regenerate its thermal barrier.

The advantage provided by the invention resides in a better use of the blades with only blades that are really damaged being sent for repair and an optimum use of the blades in service. The result is an increase in the mean time between failures or MTBF and/or of the mean time between overhaul or TBO, which results in a very substantial reduction in the overall cost of ownership of the turbine engine.

The principle of the method implemented by the invention is based on a measurement of the thickness of alumina thanks to the property possessed by the ceramic used for the thermal barriers of the blades of being transparent to visible light. The photons of visible light emitted by halogen lamps pass through the layer of ceramic 4 so as to reach the layer of alumina 3 and heat it up. Since alumina is an insulator, the heat received has a tendency to dissipate preferably on the side of the ceramic layer 4, rather than inside the layer of aluminum 2 and the substrate 1. This dissipation therefore occurs differently depending on the thickness of the layer of alumina existing in the thermal barrier and hence depending on the aging that the blade has previously undergone. The greater the aging to which it is subjected, the greater is the thickness of the layer of alumina and the more the flow of heat is directed toward the ceramic layer; the consequence of this is a higher surface temperature for the component. The measurement of the temperature on the surface of the blade by the thermal camera 12 thus gives a precise measurement of the aging previously undergone.

This method of analysis of the damage has been described with the use of visible light and using the property of transparency of the ceramic to this wavelength. It could also be implemented with radiators emitting at other wavelengths, after an adaptation of the form of the figure in FIG. 4. In the case where the ceramic were not transparent to the chosen wavelength, the dissipation of the temperature would take place in a different manner owing to the influence of the alumina and its insulating nature; the form of the curve in FIG. 4 would then also be different. In any event, the presence of a layer of variable thickness of alumina between the ceramic and the substrate will yield variations in the behavior over time of the surface temperature of the component; it will then be possible, potentially with adaptations within the capability of those skilled in the art after suitable experimentation, to analyze the behaviors over time of surface temperature and to determine, by virtue of these behaviors, the damage that has been suffered by the thermal barrier.

The invention claimed is:

1. A method for evaluating damage to a thermal barrier deposited on a metal substrate of a component, the thermal barrier including an aluminum underlayer and a layer of ceramic material with a columnar structure oriented perpendicularly to the substrate, the underlayer being positioned between the substrate and the ceramic layer, the damage being defined by thickness of oxidized metal present in the underlayer, the method comprising:

selecting a given number of calibration elements including a substrate which is covered by the thermal barrier, the calibration elements having been subjected to damage by exposure for different periods of time to oxidation conditions representative of use;

exposing, for a given period of time, the calibration elements to an electromagnetic radiation;

measuring a temperature obtained on a surface of the calibration element after the given period of time, for each calibration element;

establishing a calibration curve based on an increase in measured temperature on the surface of the calibration element to damage suffered by the calibration element, for each calibration element;

exposing an element to be evaluated to radiation for the given period of time, the element to be evaluated including a substrate which is covered by the thermal barrier;

measuring the temperature obtained on the surface of the element to be evaluated after the given period of time;

plotting, on the calibration curve, an increase in measured temperature on the surface of the element to be evaluated after the given period of time; and determining the damage of the thermal barrier of the element to be evaluated from the calibration curve based on the increase in measured temperature on the surface of the element to be evaluated.

2. The method as claimed in claim 1, wherein the element to be evaluated is a turbine blade of a turbine engine.

3. The method as claimed in claim 1, wherein at least first, second, and third calibration elements are selected, the first calibration element has a first amount of damage, the second calibration element has second amount of damage greater than the first amount of damage, and the third calibration element is free of damage.

4. The method as claimed in claim 3, wherein the increase in measured temperature on the surface of the third calibration element is greater than the increase in measured temperature on the surface of the first calibration element and of the second calibration element, and the increase in measured temperature on the surface of the first calibration element is greater than the increase in measured temperature on the surface of the second calibration element.

5. The method as claimed in claim 1, wherein the radiation is optical radiation in the visible range.

6. The method as claimed in claim 5, wherein the radiation is provided by illumination of at least one halogen lamp.

7. The method as claimed in claim 5, wherein the measuring of the surface temperatures of the calibration elements and of the element to be evaluated is carried out by a camera operating in infrared.

* * * * *